(12) United States Patent
Padalino et al.

(10) Patent No.: US 9,968,271 B2
(45) Date of Patent: May 15, 2018

(54) NEEDLE ELECTRODE SAFETY DEVICE

(71) Applicant: The Research Foundation of State University of New York, Albany, NY (US)

(72) Inventors: David J. Padalino, Liverpool, NY (US); Blair Calancie, Manlius, NY (US)

(73) Assignee: The Research Foundation of State University of New York, Albany, NY (US)

(*) Notice: Subject to any disclaimer, the term of this patent is extended or adjusted under 35 U.S.C. 154(b) by 684 days.

(21) Appl. No.: 14/381,440

(22) PCT Filed: Feb. 28, 2013

(86) PCT No.: PCT/US2013/028164
§ 371 (c)(1),
(2) Date: Aug. 27, 2014

(87) PCT Pub. No.: WO2013/130711
PCT Pub. Date: Sep. 6, 2013

(65) Prior Publication Data
US 2015/0126842 A1 May 7, 2015

Related U.S. Application Data

(60) Provisional application No. 61/606,113, filed on Mar. 2, 2012.

(51) Int. Cl.
*A61B 5/04* (2006.01)
*A61B 5/0492* (2006.01)
(Continued)

(52) U.S. Cl.
CPC ........ *A61B 5/04001* (2013.01); *A61B 5/0492* (2013.01); *A61B 5/6833* (2013.01);
(Continued)

(58) Field of Classification Search
CPC .............. A61B 17/3494; A61B 5/6833; A61B 5/04001; A61B 5/0478; A61B 5/0492;
(Continued)

(56) References Cited

U.S. PATENT DOCUMENTS 4,380,234 A 4/1983 Kamen
4,737,143 A 4/1988 Russell
(Continued)

OTHER PUBLICATIONS

Korean Intellectual Property Office International Search Report and Written Opinion of the International Searching Authority for International Application No. PCT/US2013/028164 dated Jun. 27, 2013 (11 pages).

*Primary Examiner* — Lee S Cohen
*Assistant Examiner* — Eunhwa Kim
(74) *Attorney, Agent, or Firm* — Harris Beach PLLC

(57) ABSTRACT

A needle electrode is provided incorporating a protective flap and optionally a retraction chamber. By providing an impenetrable barrier covering the area of skin over the needle's tip, the protective flap protects against needle sticks that can occur when the tip of a needle electrode is pushed back out through the skin. An adhesive layer on the skin-side of the protective flap secures the needle in place without the use of a separate piece of adhesive tape. Other types of needles can incorporate flaps for protection or for securing the needle to the patient.

16 Claims, 9 Drawing Sheets

(51) Int. Cl.
*A61B 5/00* (2006.01)
*A61B 17/34* (2006.01)
*A61B 5/0478* (2006.01)

(52) U.S. Cl.
CPC ........ *A61B 5/6849* (2013.01); *A61B 17/3494* (2013.01); *A61B 5/0478* (2013.01)

(58) Field of Classification Search
CPC ....... A61F 2013/00408; A61M 5/3134; A61M 5/1626; A61M 25/0631
USPC .................................................. 604/115, 117
See application file for complete search history.

(56) References Cited

U.S. PATENT DOCUMENTS

| | | | |
|---|---|---|---|
| 4,935,011 A | | 6/1990 | Hogan |
| 5,087,248 A | | 2/1992 | Beisang, III |
| 2007/0060892 A1 | | 3/2007 | Propp |
| 2011/0105876 A1 | | 5/2011 | Zhang |
| 2013/0237790 A1* | | 9/2013 | Riess ................... A61B 5/0478 600/373 |

* cited by examiner

NEEDLE ELECTRODE SAFETY DEVICE

CROSS-REFERENCE TO RELATED APPLICATIONS

This application is a national stage application under 35 U.S.C. § 371 of PCT Application No. PCT/US2013/028164, filed Feb. 28, 2013, which claims priority to and the benefit of U.S. Provisional Application No. 61/606,113 filed on Mar. 2, 2012, which are incorporated herein by reference in their entirety.

CROSS-REFERENCE TO RELATED APPLICATIONS

This application claims priority to and the benefit of U.S. provisional patent application Ser. No. 61/606,113, entitled "Needle Electrode Safety Device," filed Mar. 2, 2012, which is incorporated herein by reference in its entirety.

STATEMENT REGARDING FEDERALLY SPONSORED RESEARCH OR DEVELOPMENT

Not applicable.

1. TECHNICAL FIELD

The present invention relates to safety needle assemblies. The invention also relates to neuromonitoring needle electrodes.

2. BACKGROUND OF THE INVENTION

The problem of needle sticks is widespread and costly. It is estimated that there are up to 3.5 million needle sticks worldwide annually, with the average cost per needle stick injury of about $2,500. Needle sticks can lead to hepatitis B infection (22-31% chance of transmission or 66,000 cases annually), hepatitis C infection (1.8% chance of transmission or 16,000 cases annually), and HIV infection (0.3% chance of transmission or 1,000 cases annually). To protect healthcare workers from the consequences of needle sticks, the *Federal Needle Stick Safety Act* was signed in 2000 and the *Bloodborne Pathogens Standard* in 2001. These regulations were enacted in recognition of the fact that the most effective way to stop the transmission of disease by needle sticks is to prevent needle sticks, and they mandate the use of safety devices and needle-removers with any sharps or needles. Unfortunately, needle stick injuries continue to be a frequent problem.

Intraoperative neuromonitoring is used during surgery in or near the central or peripheral nervous system. It provides a valuable tool for assessing the integrity of certain neurologic pathways/tracts of a patient during surgery and helps in early identification of adverse events intraoperatively. Every case of intraoperative neuromonitoring typically requires placement of 16-32 subdermal needle electrodes. In practice, the needle electrodes are thin and shallowly placed, and remain in place during surgery. They are generally removed after the operation.

Patients are often repositioned for transport or other reasons while the neuromonitoring needles are still in place. Needle tips can, and often do, re-emerge through the skin during moving, repositioning and handling of the patient. Many patients, especially the elderly, have thin skin, making it easier and more likely that a needle electrode will re-emerge.

Numerous needle stick injuries have been reported from neuromonitoring needle electrodes, generally occurring at the time of patient transfer between the stretcher and the operating room (OR) table, or during and after the removal of the needles following surgery. In fact, the inspiration for the present invention was the inventor's awareness that every neuromonitoring tech and many other healthcare workers involved in the care of monitored patients with whom he has worked had suffered at least one needle stick injury from a neuromonitoring needle electrode, including a pregnant neuromonitoring tech who had a needle stick injury from an unprotected needle electrode while monitoring an HIV+ patient.

Retraction chambers into which a needle can be withdrawn during or after removal from a patient have been used to protect healthcare workers from many other types of needles, and a needle electrode with a retraction chamber has been suggested (ref. US patent application publication no. 20110105876). However, needle retraction chambers solve only the problem of protecting the healthcare worker from needle sticks after the needle is removed, not while the needle is still in the patient.

When needles are placed in a patient, such as for neuromonitoring, IV drips or blood withdrawal, a piece of adhesive tape is often employed to anchor the needle in place and prevent it from being unintentionally pulled out. There are several problems with the use of adhesive tape. First, a healthcare worker needs to tear an appropriate length of the adhesive tape strip in advance, or remove both hands from the needle and patient to tear off a piece after the needle is placed. Second, the tape is placed over the needle's connecting hub or the exposed portion of the needle or cannula, placing a downwards pressure on the base end of the needle assembly, a force which effectively translates, with the point of entry in the skin as a fulcrum, into an upward force on the tip of the needle or cannula. And third, removal of the adhesive tape and of the needle are separate, sequential operations. What is needed is a better way of securing a cannula or needle to a patient.

Citation or identification of any reference in Section 2, or in any other section of this application, shall not be considered an admission that such reference is available as prior art to the present invention.

3. SUMMARY OF THE INVENTION

One aspect of the present invention is a needle assembly (with or without cannula) incorporating a protective flap that is attached at the base of the needle, such as to the needle/wire connector or wire of a needle electrode, to a connecting hub, or to a retraction chamber or safety cover. The protective flap extends beyond the tip of the needle, providing an impenetrable barrier between needle tip and medical personnel. In a preferred embodiment, the protective flap is transparent so that the needle entry site is visible.

In one embodiment, the protective flap is secured to the skin after needle placement by an adhesive layer on at least a portion of the skin-side of the flap. Preferably the adhesive layer is covered prior to use by a removable or peel-away strip, and the adhesive layer is exposed by removing the peel-away strip. The adhesive holds the protective flap in place over the tip of the needle (or trocar) and also secures the needle assembly or cannula to the patient without applying pressure to the exposed portion of the needle assembly. To remove the needle, the protective flap is simply peeled off the patient; a tab on the free end of the flap can be provided to make this easier. The protective flap can also have a fracture or tear point at which it will separate from the needle assembly under appropriate circumstances such as a sharp yank on the needle assembly or something attached to it (e.g., a wire).

In one embodiment, the present invention also incorporates a retraction chamber into which the needle can be withdrawn as it is being removed, or after its removal from the patient. The protective flap is preferably attached to the retraction chamber. When removing the needle from the patient, the needle is withdrawn into the retraction chamber and then, if it has an adhesive side, the flap is peeled off the patient. If the needle is drawn into the retraction chamber by pulling on a wire or tube attached to the base end of the needle, a strip of material can be attached to the wire or tube at one end and to the free end of the protective flap at the other so that the protective flap will be peeled back as the needle is withdrawn into the retraction chamber.

One aspect of the present invention is a safety needle assembly which comprises a needle having a base end and a tip, a body attached at a first end to the base end of the needle, and a flap attached at a first end to the body, the flap having a second distal free end capable of extending beyond the tip of the needle. The needle is of any type, such as a needle electrode or an IV needle, especially those that are left for some period of time after being placed in a patient, and can be solid or hollow (generally tubular).

The body may be fluidically or electrically connective, providing a fluid connection to a tube or an electrical connection to an electrically conductive wire. The body may incorporate a valve or switch. In one embodiment, the body can comprise (or consist of) an electrical connector and a wire and the needle is a needle electrode, and the flap is movably attached to the body. In one embodiment, the needle is hollow, the body is a tube connected fluidically to the hollow needle at one end and fluidically to a connector at the other end adapted for connecting fluidically with another tube, optionally with a valve at the other end. In one embodiment, the flap is pre-creased so that pressing on a portion of it will cause another portion of the flap to move such that the needle's tip more accessible.

In any of the preceding embodiments, the flap can incorporate an adhesive layer, preferably with a cover strip over the adhesive, on its side that will be adjacent to the patient's skin when the flap is extended over the point of needle entry into the patient. The cover strip over the adhesive can be adapted to make removal easier, such as by incorporating a tab or by incorporating a pull strip.

In any of the preceding embodiments, the flap can be entirely or partly constructed from a material that is needle-pierce resistant, with at least the portion of the flap that is, or can be made to be, over tip of the needle made of such pierce-resistant material. The area covered by the needle-pierce resistant material should cover an area about the shape of a circle or oval or rounded edge shape with a radius equal to about the length of the exposed portion of the needle, and should be roughly centered over the needle tip when it is positioned above and substantially parallel to the needle, in order to provide a barrier at any point that can be reached by the needle tip in the event of the needle tip re-emerging through the skin.

The preceding embodiments can comprise a safety needle assembly comprising a needle, a body attached at a first end to a base end of the needle, a safety cover movably attached to the body, and a flap attached at a first end to the safety cover, the flap having a second distal free end capable of extending beyond the tip of the needle.

Another aspect of the present invention is a method of protecting against needle sticks caused by a needle tip re-emerging from a patient's body having the steps of positioning a patch of pierce-resistant material over a sharp tip of a needle after the needle's sharp tip is placed into the patient's body. In one embodiment, the needle is part of a needle assembly, and the patch of pierce-resistant material is attached the needle assembly. In one embodiment, the method also has the step of securing the pierce-resistant patch of material to the patient using an adhesive. In one embodiment, the adhesive is in a layer on a portion of one side of the flap. In another, the adhesive is part of a separate tape that is used to secure the flap to the patient. One optional step in the method is removing a cover strip from the adhesive on the flap.

One aspect of the present invention is a safety needle assembly comprising a needle, a connector, and a safety cover or retraction housing, within a central cavity of which is movably disposed the connector, the connector attached at the first end to a base end of the needle. The central cavity is slightly larger in its internal cross-sectional dimensions than the connector. The safety cover's central cavity is of sufficient length to cover the connector and the needle when the connector and needle are pulled or withdrawn fully into it. Attached to a second end of the connector is a wire or tube. The safety cover has a slot in its side into which protrudes a spring-loaded catch which can be depressed by finger pressure into the central cavity where it will prevent movement of the connector relative to the safety cover (or in one embodiment, pressure will raise the catch so that it ceases to prevent movement of the connector relative to the safety cover). Optionally, there is a flap attached to the inner wall of the safety cover central cavity proximal to a first open end of the safety cover proximal to the needle tip which is held open by the connector when the needle is extended from the safety cover but which falls or springs out to cover the open end of the safety cover once the connector and needle are pulled into the safety cover.

In another embodiment, an apparatus is provided comprising a needle electrode for neuromonitoring protruding from a protective retraction chamber housing into which the needle can be retracted for shielding the tip of the needle electrode. There can be a piece of clear, durable but flexible polymer material formed into a flap which overlies the protruding portion of the needle electrode and which functions to provide a protective cover over the top of the protruding needle electrode tip during use.

In another embodiment, the electrode needle-wire connection interface receives at least a portion of the needle tip shield housing.

In another embodiment, the apparatus can comprise a needle friction lock feature to inhibit movement of the needle electrode along the central axis of the retraction chamber during insertion of the needle electrode.

In another embodiment, the lock feature comprises a spring-loaded button or spring lever or friction mechanism which is engaged to prevent retraction of the needle electrode into the retraction chamber while an external button is depressed or the retraction chamber housing is manipulated.

In another embodiment, the lock feature is integrated with the retraction chamber such that the lock feature selectively abuts the needle electrode-wire connection interface region to maintain the position of the needle.

In another embodiment, the inner region of the retraction chamber comprises a flap element to retain the end of the needle electrode within the inner cavity upon fully retracting the needle beyond the distal opening, and preventing the needle tip from returning to the position P1 through this distal opening once retracted to the position P2.

In another embodiment, the protective flap has an adhesive layer on the undersurface which is exposed upon removal of a protective film, allowing the flap to be used to secure the inserted needle into position once inserted into the patient.

4. BRIEF DESCRIPTION OF THE DRAWINGS

The present invention is described herein with reference to the accompanying drawings, in which similar reference characters denote similar elements throughout the several views. It is to be understood that in some instances, various aspects of the invention may be shown exaggerated or enlarged to facilitate an understanding of the invention.

5. DETAILED DESCRIPTION OF THE INVENTION

A safety needle assembly is provided.

Figure 1A:
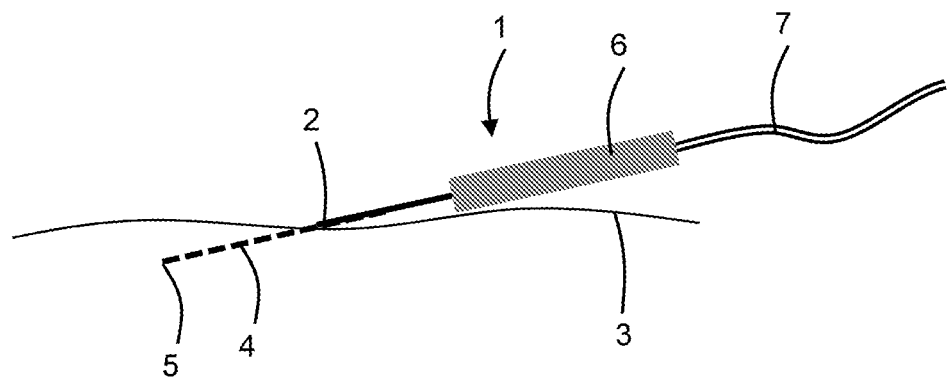
FIG. 1A is a plane view drawing of a prior art needle placed in the skin of a patient.
Figure 1B:
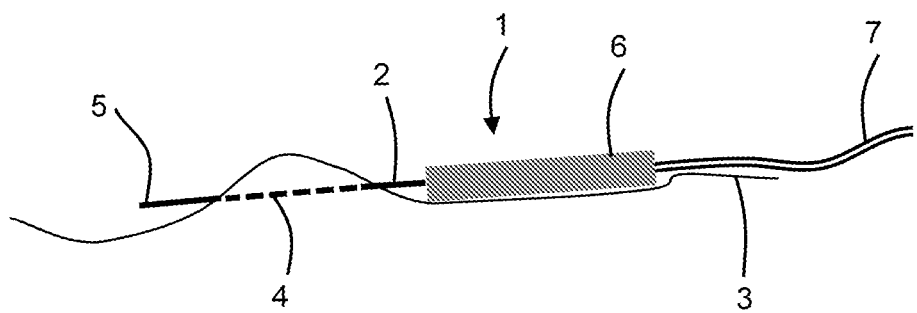
FIG. 1B is a plane view drawing of the tip of a prior art needle re-emerging through the skin of a patient.

FIG. 1A shows a prior art neuromonitoring needle assembly in place in a patient. The neuromonitoring needle assembly can comprise (or consist of) a needle electrode 2 electrically connected to a wire 7 by an electrical connector 6. The needle electrode 2 is placed subdermal in a patient's skin 3. A portion (dotted) of the needle electrode 4 is under the surface of the skin 3, with the sharp tip of the needle 5 safely under the skin. FIG. 1B shows what can happen when a prior art neuromonitoring needle 1 is disturbed, such as when a patient is moved while the neuromonitoring needle assembly 1 is in place. The needle electrode 2 and the surrounding skin 3 can be disturbed sufficiently that the sharp tip of the needle 5 can re-emerge through the skin 3, creating a needle stick hazard.

Figure 2A:
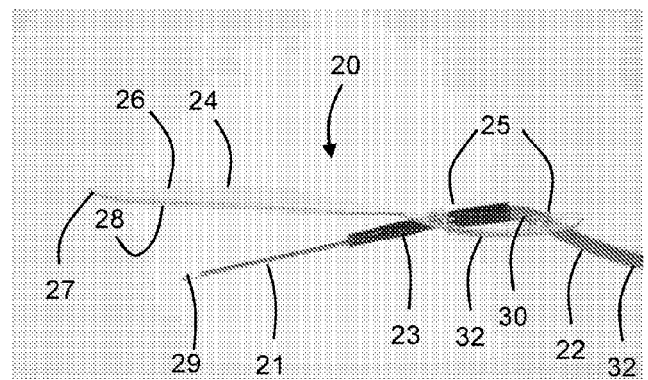
FIG. 2A is a side view photo of a neuromonitoring needle electrode having a protective flap.
Figure 2B:
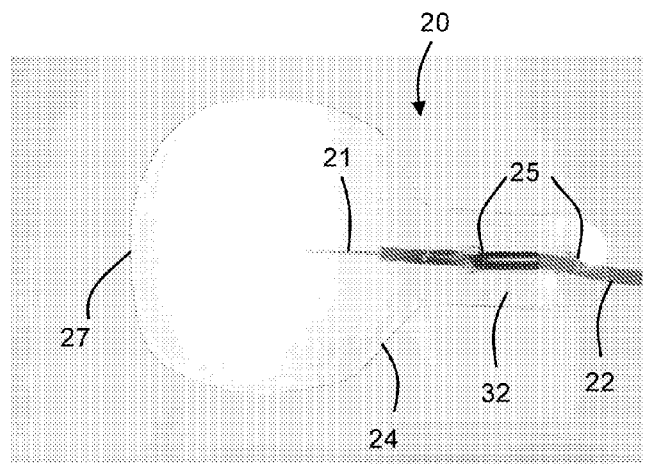
FIG. 2B is a top view photo of a neuromonitoring needle electrode having a protective flap.
Figure 2C:
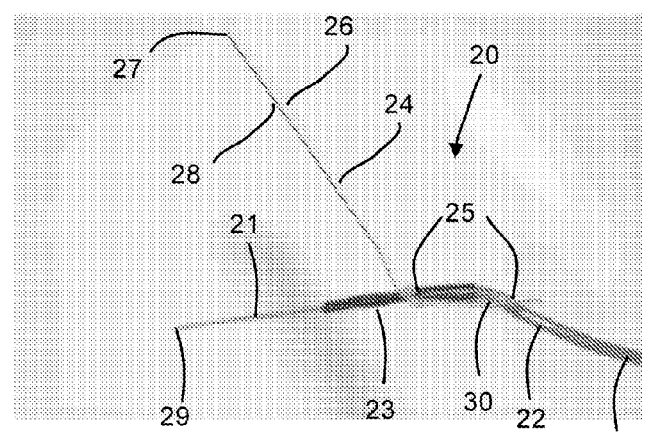
FIG. 2C is a side view photo of a neuromonitoring needle electrode having a protective flap showing how the flap can be folded back to fully expose the needle.

FIGS. 2A-2C show a safety needle assembly 20 configured in accordance with an embodiment of the present invention. The safety needle assembly 20 can comprise (or consist of) a needle 21 (in the figure, the needle 21 is a neuromonitoring needle electrode), connected electrically to a proximal end 30 of a wire 22, with a connecting electrode-wire interface sheath 23 covering the connection point, and a protective flap 24. The distal end 27 of the protective flap 24 extends beyond the free, sharp tip 29 of the needle 21 to provide a barrier between the sharp needle tip 29 and a healthcare worker. The protective flap 24 is transparent to allow the needle 21, and the needle entry point at the skin, to be visible (in FIG. 2B, the needle electrode 21 is behind the protective flap 24 but is still visible).

The protective flap 24 is secured to the wire 22 and sheath 23 by passing the wire 22 through two mounting holes 25 formed in the base end 32 of the protective flap 24. It can be secured by other means such as by wrapping a portion of the base end 32 of the protective flap 26 around the wire 22 and/or sheath 23 to form a tube through which the wire 22 can pass. The protective flap 24 can be fixed to the wire 22 so that the two cannot move relative to one another, or it can be more loosely attached so that the wire 22 and needle 21 can be pulled free of the protective flap 24. In one embodiment, when the safety needle assembly 20 is not in use, the needle 21 rests against and parallel to the flap 24.

FIG. 2C shows how the protective flap 24 can be pulled up and away from the needle 21 to make it easier to place the needle 21 into a patient. The protective flap 24 can be designed to be able to be bent completely back to the wire 22 to be completely clear of the needle 21.

The protective flap 24 has a top surface 26 that will face away from the patient when the needle 21 is in place, and an opposite, bottom, skin-facing surface 28 (not visible). In one embodiment, there is adhesive on the skin-facing surface 28 of the flap 24 covered by a peel-away cover (not shown). Once the needle 21 is placed in the patient, the peel-away cover over the adhesive layer on the skin-facing side 28 (e.g., the peel-away paper or plastic covering the adhesive ends of an adhesive bandage before use) is removed, exposing the adhesive layer, which is then pressed down onto the patient's skin, securing protective flap 24, and therefore also the safety needle assembly 20, to the patient. If the protective flap 24 is attached loosely to or surrounding the wire 22, a medical tech can remove the needle electrode 21 simply by pulling on a free section 32 of the wire 22 (i.e., the part away from the electrode-wire interface sheath 23) as is currently often done, thereby pulling the needle 21 out of the patient and out through the holes 25 in the protective flap 24, leaving the protective flap 24 still attached to the patient's skin, to be removed later. If the protective flap 24 is attached fixedly to the wire 22, the protective flap 24 may have to be peeled away before the safety needle assembly 20 can be removed.

In one embodiment there is a tab which does not have an adhesive layer situated at the distal end 27 of the protective flap 24 which provides a gripping surface which medical personnel can grasp to peel back and remove the protective flap 24 from the patient's skin. In an alternate embodiment, the protective flap 24 is constructed of two pieces that will separate under the force of a technician pulling on the wire 22 to remove the needle; preferably such separation will require more force than the inadvertent tugs on the wire that may occur accidentally during a procedure as medical personnel brush up against or move the patient. In an alternate embodiment, a base section of the flap 24 is fixedly attached to the wire 22 or wire connector 23, and there is a weak point (such as a crease or a line of perforations) in the protective flap 24, in its base end 32, or between the base section 32 and the section of the flap 24 that attaches to the patient. A sharp pull on the wire 22 by the medical personnel will cause the protective flap 24 to break at the weak point and separate into two parts, the base section remaining attached to the wire 22 and coming away with the needle 21, and the rest of the protective flap 24 remaining attached to the patient's skin for later removal.

Figure 3:
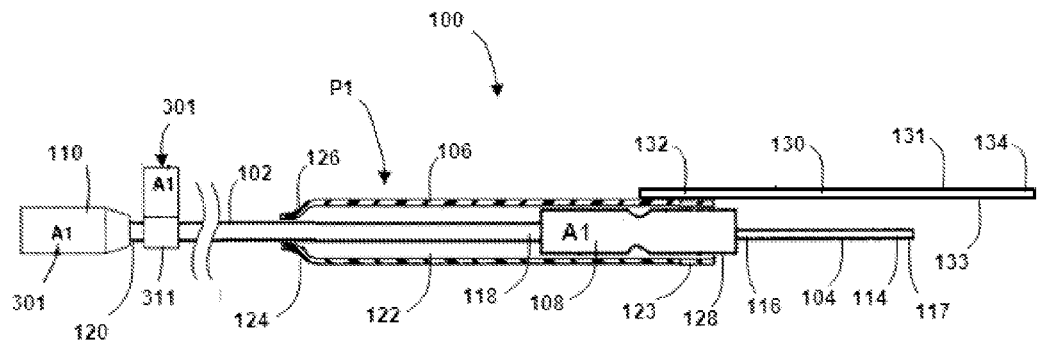
FIG. 3 is a partial cross-sectional side view showing a subdermal needle electrode cable assembly configured in accordance with an embodiment of the present invention, wherein a safety cover is in its initial position with respect to a needle electrode of the subdermal needle electrode cable assembly.
Figure 4:
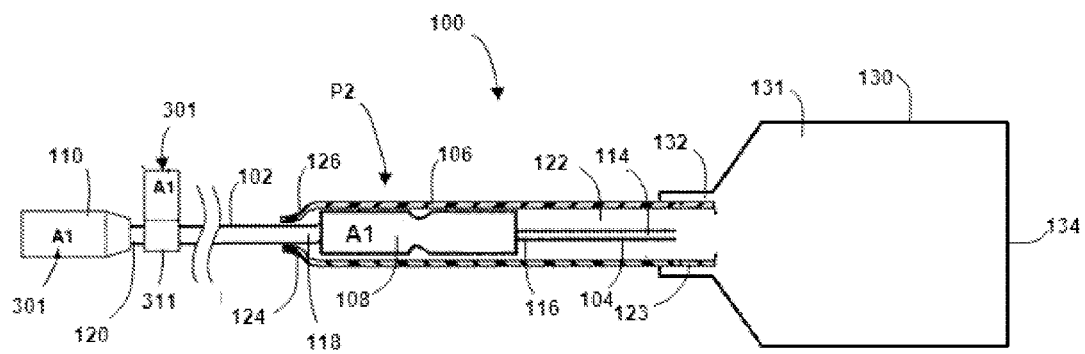
FIG. 4 is a partial cross-sectional bottom view of the subdermal needle electrode cable assembly shown in FIG. 3 wherein the safety cover is in a needle concealing position.

FIGS. 3-4 show a subdermal needle electrode cable assembly 100 configured in accordance with an embodiment of the present invention. The subdermal needle electrode cable assembly 100 is an example of an apparatus configured in accordance with the present invention for monitoring neurological and/or neurophysiological signals of a patient. Examples of such signals include, but are not limited to, electroencephalogram (EEG) signals, spontaneous or triggered electromyogram (EMG) signals, somatosensory evoked potential (SSEP) signals, transcranial motor evoked potential (tcMEP) signals, brainstem auditory evoked potential (BAER) signals, and visual evoked potential (VEP) signals.

The subdermal needle electrode cable assembly 100 includes a lead wire 102, a needle electrode 104, a retraction chamber or safety cover 106, a first electrical connector (in one embodiment, a needle electrode-wire junction) 108, a second electrical connector 110 (in one embodiment, a standard neuromonitoring wire plug), and a needle cover (not shown) which is removably secured over a first end portion 114 (which includes the needle tip) of the needle electrode 104 for concealing the first end portion 114 of the needle electrode 104 prior to its use, and which can attach to the safety cover 106 or the exposed end 128 of the first electrical connector 108 by any known means, such as friction or screw threads. Until the needle cover is removed from its secured position over the first end portion 114 of the needle electrode 104, the safety cover 106 is preferably inhibited from being moved along the length of the lead wire 102 toward the first end portion 114 of the needle electrode 104 thereby causing the first end portion 114 of the needle electrode 104 to become positioned within the central passage 122 of the safety cover 106.

The needle electrode 104 has a first end portion 114 and a proximal needle segment 116. The first end portion 114 of the needle electrode 104 is configured for piercing skin of a patient. For example, the first end portion 114 of the needle electrode 104 can be sharpened. Straight needle electrodes and hook needle electrodes are two known types of needle electrodes. The lead wire 102 has a first end portion 118 and a second end portion 120. The first electrical connector 108 is electrically connected to a second end portion 116 of the needle electrode 104 and the first end portion 118 of the lead wire 102 for providing electrical continuity between the needle electrode 104 and the lead wire 102. A second electrical connector 110 is connected to the second end portion 120 of the lead wire 102 for allowing the subdermal needle electrode cable assembly 100 to be electrically connected to signal monitoring equipment used in monitoring neurological and/or neurophysiological signals. In general, a typical procedure in which monitoring of neurological and/or neurophysiological signals of a patient is performed will require a plurality of subdermal needle electrode cable assemblies to be connected between the patient and the signal monitoring equipment.

It is disclosed herein that the first electrical connector 108 and the second electrical connector 110 can each include an electrically insulating cover and an electrically conductive element with the electrically insulating cover. Similarly, the lead wire 102 can include an electrically insulating cover with an electrically conductive core extending the length of the electrically insulating cover (i.e., an insulated single strand or multi-strand wire). In the case of the first electrical connector 108, the electrically conductive element is electrically connected to both the needle electrode 104 and to the electrically conductive core of the lead wire 102 (e.g., by means such as crimping, mechanical interference, soldering, ultrasonic welding, or the like). In the case of the second electrical connector 110, the electrically conductive element is electrically connected to the electrically conductive core of the lead wire 102 and is configured for being removably engaged with (such as plugged into) a signal receiving terminal or port of the signal monitoring equipment.

Preferably, but not necessarily, an exterior surface of the first electrical connector 108 is brightly colored (e.g., bright orange, florescent green, etc) and/or has an otherwise very distinctive visual appearance (e.g., multi-color pattern). Such distinctive visual appearance adds a visual safety warning of the needle electrode 104 when it is implanted and subsequently removed for collection and disposal. In this manner, subdermal needle electrode cable assemblies 100 configured in accordance with the present invention can be configured for enhancing attention to the needle electrodes thereby reducing the potential for needle stick incidents.

The safety cover 106 is slideably (i.e., moveable) mounted on the lead wire 102. The lead wire 102 extends through a central passage 122 of the safety cover 106. The safety cover is movable between a first position P1 (FIG. 3) in which at least the first end portion 114 of the needle electrode 104 is exposed outside of the central passage 122 and a second position P2 (FIG. 4) in which an entire portion of the needle electrode 104, including its end configured for piercing, becomes positioned within the central passage 122. In this manner, the central passage 122 is sized and/or otherwise configured to receive the first connector 108 and the needle electrode 104 therein, thereby providing a needle electrode shrouding space that extends through a first end portion 123 of the safety cover 106.

The central passage 122 includes a reduced cross sectional portion 124 at a second end portion 126 of the safety cover 106. The reduced cross sectional portion 124 causes the safety cover 106 to engage the first electrical connector 108 for defining a maximum amount of displacement of the safety cover 106 with respect to the needle electrode 104 when the safety cover 106 is being moved toward the first end portion 114 of the needle electrode 104 (or alternately when the needle electrode 104 and first electrical connector are moved into the safety cover 106). The reduced cross sectional portion 124 is one example of a means for defining a maximum amount of displacement of the safety cover 106 with respect to the needle electrode 104. It is disclosed herein that other such means can be implemented in place of or in conjunction with the reduced cross sectional portion 124. Examples of such means include, but are not limited to, one or more protrusions within the central passage 122, an end cap with a hole therein attached to the second end portion 126 of the safety cover 106, and the like.

A subdermal needle electrode cable assembly 100 can include identifying information 301 on the first electrical connector 108, the second connector 110, and/or on an identification-carrying structure 311 that is fixedly attached to a lead wire 102 thereof. The identifying information 301 can include alphanumeric identifying information (e.g., A1), color-coded identifying information (e.g., A1 is a designated color), or both. When the subdermal needle electrode cable assembly 100 is part of a set of subdermal needle electrode cable assemblies, such identifying information 301 is useful in identifying the subdermal needle electrode cable assembly 100 (i.e., the needle electrode thereof) with respect to each other one of the subdermal needle electrode cable assemblies 100 of the set. In one example, such a set of subdermal needle electrode cable assemblies 100 is in the form of a cable unit. In another example, such a set of subdermal needle electrode cable assemblies 100 is in the form of a plurality of individual subdermal needle electrode cable assemblies 100. By using the same identifying color or notation for both ends of the subdermal needle electrode cable assemblies 100 (for example for both the first 108 and second 110 connectors), medical personnel will easily be able to determine which needle 104 is electrically connected to which second connector 110, even if the wire 102 is long (e.g., one or more meters).

It is disclosed herein that the safety cover 106 can be configured for limiting or precluding unintentional movement toward the first position P1 once it is in the second position P2 (i.e., an entire portion of the needle electrode 104 becomes positioned within the central passage 122). In one embodiment, the reduced cross sectional portion 124 of the central passage 122 and the lead wire 102 are jointly configured whereby friction therebetween provides for limiting or precluding unintentional movement of the safety cover 106 toward the first position P1 once it is in the second position P2. In another embodiment, the central passage 122 and the first electrical connector 108 are jointly configured to limit or preclude unintentional movement of the safety cover 106 toward the first position P1 once it is in the second position P2. For example, the central passage 122 and the first electrical connector 108 can be jointly configured whereby friction therebetween limits or precludes unintentional movement of the safety cover 106 toward the first position P1 once it is in the second position P2, the central passage 122 and/or the first electrical connector 108 can include a mechanical interlock structure that limits or precludes unintentional movement of the safety cover 106 toward the first position P1 once it is in the second position P2, etc. It is disclosed herein that the present invention is not unnecessarily limited to any particular means for limiting or precluding unintentional movement of the safety cover 106 toward the first position P1 once it is in the second position P2. For example, the resiliency/flexibility of the lead wire 102 can be sufficient to limit or preclude unintentional movement of the safety cover 106 toward the first position P1 once it is in the second position P2.

Figure 5A:
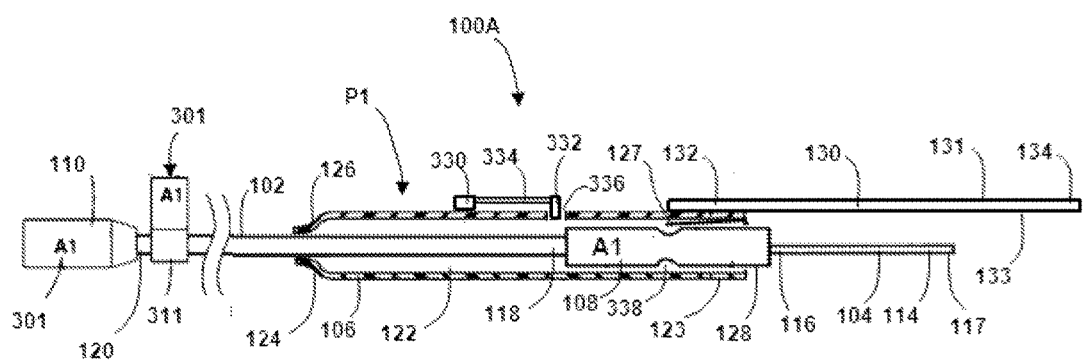
FIG. 5A is a partial cross-sectional side view showing a subdermal needle electrode cable assembly configured in accordance with an embodiment of the present invention incorporating a catch for preventing movement of the needle when inserting it into a patient and a needle stop flap to close the safety cover after the needle is retracted into it.
Figure 5B:
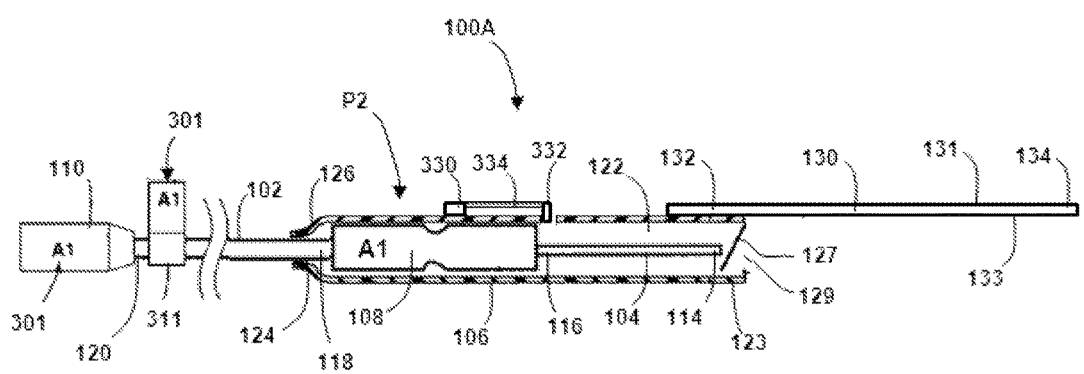
FIG. 5B is partial cross-sectional side view of the subdermal needle electrode cable assembly shown in FIG. 10, wherein the needle is in a retracted position and the needle stop flap is covering the open end of the safety cover to prevent the needle from re-emerging and to protect against a needle stick.

The needle electrode assembly 100A shown in FIGS. 5A and 5B is the same as the needle electrode assemblies 100 shown in FIGS. 3 and 4 with two changes. The needle electrode assembly 100A incorporates a user depressable catch 332 for preventing the safety cover 106 from moving from the first position P1 to the second position P2 while the needle 114 is being inserted into a patient. The catch 332 is attached to a spring arm 334 which is mounted to a protrusion 330 on the safety cover 106. Adjacent to the catch 332 is a hole or slot 336 through the safety cover 106 proximal to its midpoint which is large enough to admit the catch 332. The spring arm 334 holds the catch 332 in a position where it does not interfere with the movement of the safety cover 106 relative to the first electrical connector 108 and needle 114. Pressing on the spring arm 334 or the catch 332 pushes the catch 332 through the slot 336 and into a position where the catch 332 will interfere with the movement of the first electrical connector 108 relative to the safety cover 106. The catch 332 and slot 336 could be positioned elsewhere along the length of the safety cover, with the catch 332 engaging with a notch 338 in the first electrical connector 108, pressing against the first electrical connector 108, or pressing on the first end portion 118 of the wire 102.

The needle electrode assembly 100A also incorporates a needle stop flap 127 at the first end portion 123 of the safety cover 106, attached to its inner wall proximal to the opening 129. The needle stop flap 127 is shown in a first position in FIG. 5A when the needle 104 is in the first position P1, where it is folded back into the safety cover's central passage 122 between its inner wall and the first electrical connector 108. Movement of needle 104 and first electrical connector 108 from the first P1 to the second position P2 releases the needle stop flap 127 so that it can spring into a second position across the open end 129 of the safety cover 106 (shown in FIG. 5B). The needle stop flap 127 is long enough, and is made of a stiff enough material, that it cannot spring past the open end 129 of the safety cover 106, but gets caught against the inner wall of the safety cover 106. In this second position, the needle stop flap 127 will block the first end portion 114 and its sharp tip 117 from re-emerging from the safety cover 106. The needle stop flap 127 can have a circular shape with a narrow tab extending from its edge for use in mounting it to the inner surface of safety cover 106.

In one embodiment, the catch 332 in its rest position is fully into the slot 336 and engaged with the first electrical connector 108, and pressing on the spring arm 334 causes the catch to disengage from the first electrical connector 108 and withdraw into the slot 336 far enough to allow the first electrical connector 108 to pass from the first position P1 to the second, retracted position P2. When pressure on the arm 334 is released, the catch 332 will push back through the slot 334 and engage with the front section of the first electrical connector 108 adjacent to the second end portion 116 of the needle 104, keeping it from moving towards the first position P1. In this embodiment, the needle stop flap 127 is optional.

The means described above can be sufficient to prevent the safety cover 106 from moving from the first position P1 to the second position P2 while the needle electrode 104 is being placed into the patient. Alternatively, if it is desired that the needle electrode 104 and first electrical connector 108 be able to slide freely relative to the safety cover 106, the safety cover 106 can be sufficiently elastically deformable that when a healthcare worker grips the safety cover 106 between their fingers, either sufficient pressure will be transferred directly to the first electrical connector 108 or wire 102 within the safety cover 106 to prevent movement, or the central passage 122 will be sufficiently deformed to prevent the first electrical connector 108 from moving within the central passage 122. Alternately, the safety cover 106 can have at least one slot in its side between its first end portion 123 and its second end portion 126, and the first electrical connector 108 can have side extension or fin that fits into and extends out through the slot. Medical personnel can hold the assembly 100 in his/her fingers, placing one finger over the safety cover 106 where the fin extends out of the slot, thereby pressing on the fin to prevent the fin, and therefore the first electrical connector 108 and needle 114 from moving. The slot is long enough that the needle electrode 104 and first electrical connector can be in the first position P1 or the second position P2, and able to move between the two. A catch can be provided in the slot or on the outer surface of the safety cover 106 past which the fin can be moved in a direction towards the second end portion 126 of the safety cover 106, but which prevents the fin, once past the catch, from moving back towards the first end portion 123 of the safety cover 106. A plurality of slots can be provided in the safety cover 106, along with a plurality of fins on the first electrical connector 108 aligned with the slots.

Fixedly attached to the first end portion 123 of the safety cover 106 is a first end portion 132 of a protective flap 130. Its broad free distal second end portion 134 extends beyond the tip 117 of the first end portion 114 of the needle electrode. The protective flap 130 can have various shapes (rectangular, trapezoidal circular, oblong, triangular, polygonal), provided that the part of the protective flap 130 that will be over the needle electrode 104 is large enough to cover the area of skin through which the tip of the first end portion 114 of the needle electrode 104 may re-emerge. To be large enough, the distal end 134 of the protective flap 130 must extend some distance beyond the tip of needle electrode 104 (for example, 0.25, 0.5, 0.75, 1, 1.5 or 2 times the length of the needle electrode 104, or for example, 1, 2, or 3 cm), and it must be wide enough that twisting of the needle assembly 100 will not allow the first end portion 114 to re-emerge from the skin beyond the edge of the protective flap 130 (for example, 0.25, 0.5, 0.75, 1.0, 1.25, 1.5, 2 times the length of the needle electrode 104, or for example, 1, 2, or 3 cm). The protective flap 130 is preferably centered laterally on the needle electrode 104 (transverse to the axis of the needle electrode 104) to protect against the needle being twisted to either side. The protective flap 130 has a first side 133 ("skin side") and a second side 131 ("outer side").

The protective flap 130 can be secured to the safety cover 106 by any known means such as by crimping, mechanical interference, adhesive, soldering, ultrasonic welding, or the like. Referring to one embodiment of the protective flap shown in FIG. 6A, protective flap assembly 141, two triangular openings 146 are cut proximal to the first end portion 142 of the protective flap 140 into the opposing lateral sides of the protective flap 140, forming two flaps 144 which extend laterally at the first end portion 142 of the protective flap 140 from a narrow neck 148 centered around its longitudinal axis proximal to the first end portion 142. To attach the protective flap assembly 141 to the safety cover 106, the flaps 144 at the first end portion 142 of the protective flap 140 are wrapped around the outer circumference of the safety cover 106, preferably proximal to its first end portion 123, and secured by any known means such as by welding or adhesive or the like. The protective flap 140 may be crimped or perforated across the narrow neck 148 to form a hinge 149 (location where bending of the protective flap 140 will preferentially occur). The protective flap assembly 141 can replace the protective flap 130 in any of the subdermal needle electrode cable assembly 100 shown herein. The dashed line shows the extent of the adhesive layer 154 that is not visible in this view of the present invention, and is included only for clarity. A second free end portion 151 of the protective flap 140 is not attached to the needle assembly 100 and can move relative to it within the constraints imposed by the protective flap's 140 first end portion 142 being attached to the needle assembly 100.

The protective flap 130 can be rigid or flexible. In order to provide protection from needle sticks it must resist piercing by the tip 117 of the needle electrode 104. It is preferably made of a somewhat flexible polymer, although it can be made of any material sufficiently resistant to piercing by a needle. The protective flap 130 is preferably transparent or semi-transparent so that the site where the electrode needle 114 enters the patient's skin can be seen through the protective flap 130. Preferably the protective flap 130 can be bent backwards away from the needle 104 so that the needle 104 is easily visible to the medical personnel while placing the needle in the patient.

Figure 6A:
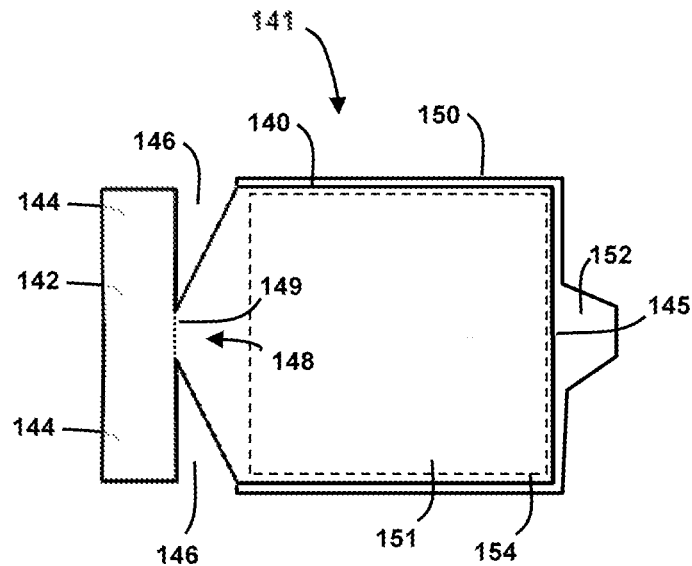
FIG. 6A is a planar top view of a protective flap assembly of the present invention.
Figure 6B:
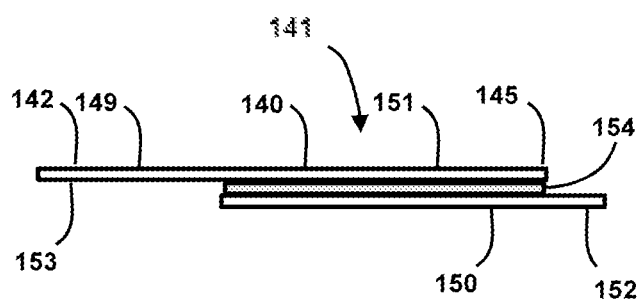
FIG. 6B is a planar side view of the protective flap assembly shown in FIG. 6A.

The protective flap assembly 141 is also shown from the side in FIG. 6B. A sticky adhesive layer 154 (similar to that on adhesive bandages and tape) is applied to the skin-side 153 of the protective flap 140 extending from the distal end 145 of the protective flap 140 to approximately where the triangular openings 146 begin in its lateral sides (the dotted square in FIG. 6A shows the extent of the adhesive layer 154 which is not visible because it is on the other side, behind the protective flap 140). Covering the adhesive layer 154, to keep it clean and sticky until use, is a removable protective strip 150 which extends slightly beyond the adhesive layer 154 on all sides. In FIG. 6A the edge of the removable protective strip 150 is visibly extending beyond the edge of the protective flap 140 on three sides. For ease of use (i.e., for removing the protective strip 150 covering from the adhesive layer 154), a tab 152 is formed in the middle of the end of the removable protective strip 150 proximal to the distal free end 145 of the protective flap 140 which extends beyond both the adhesive layer 154 and the protective flap 140. Once the electrode needle 104 is in place in the patient, the healthcare worker can remove the removable protective strip 150 by grasping the flap 152 and peeling the protective strip 150 back. The adhesive layer 154 can cover more or less of the protective flap 140, for example only covering a small portion of the protective flap 140 proximal to the distal end 145 of the protective flap 140 (e.g., the final 0.25, 0.5, 1.0, 1.5, 2.0 or 3 cm of the protective flap 140). In an alternate embodiment, the tab 152 extends from one of the lateral sides of the protective flap 140.

In one embodiment, the protective flap 140 attached to the needle assembly 100 at its first end portion 142 with its second end portion 151 extending from the first end portion 142 away from the first end portion 114 of the needle 104. The adhesive layer 154 is on the side of the protective flap facing away from the needle assembly 100. In this embodiment, the protective flap 140 does not obstruct the needle 104. Medical personnel place the needle 104 in the patient, remove the adhesive cover strip 150, and then bend the protective flap 140 toward the needle 104, pressing the now uncovered adhesive layer 154 down onto the patient's skin above the needle 104 to secure it. The protective flap 140 can be pre-bent at the narrow neck 148 such that a hinge 149 will be formed at the narrow neck 148 and the second end portion 151 of the protective flap 140 will tend to spring away from the longitudinal axis of the needle assembly 100 (this will generally be aligned with the central axis of the cylindrical needle) to a rest position where the second end portion 151 of the protective flap 140 is at an oblique angle to the longitudinal axis of the needle assembly 100 and the first end portion 142 is attached to the needle assembly 100. This angle is preferably between about 30 and 90 degrees (making it easier for a person to grasp the needle assembly 100 without having to actively lift the protective flap) or between about 90 and 135 degrees (making it easier to see the needle without having to actively pull back on the protective flap).

In one embodiment of the present invention, the protective flap assembly 141 comprises only the second end portion 151 and is not intended to be attached to a needle assembly. In this embodiment, after a needle is placed into a patient, the protective flap 140 is placed on the patient's skin roughly centered above the estimated location of the needle's sharp tip, with its adhesive side 153 down (after the cover strip 150 has been removed by the medical personnel). The protective flap assembly 141 may incorporate a tab with no adhesive on it to make removal easier. If the protective flap 140 comprises a pierce-resistant portion and a portion that is not pierce resistant, the pierce resistant region should be centered above the estimated position of the needle tip.

The protective flap 130 can be made of multiple materials, with at least a first section of needle pierce resistant material that covers an area over the tip 117 of the needle electrode 104, and a second section of a highly flexible material which is attached to the first connector 108 or the safety cover. For example, the first section can be constructed of a somewhat rigid polymer (and made thick enough to resist needle piercing) such as those used in disposable drink bottles and in clear containers for vegetables and berries, and the second section can be made of a thin very flexible polymer such as that used in adhesive bandages or a woven fabric such as that used for athletic tape or duct tape. In one embodiment, the second section surrounds the first section, and only the second section has adhesive on a portion of it; the second section adheres to the patient's skin and holds the protective first section of the protective flap in place. The protective first section of the protective flap embodiment made of multiple materials preferably covers an area above the needle tip that is at least the size of a circle 1 cm, 2 cm, 3 cm or more in diameter that is preferably centered over the needle tip 117 when the protective flap 140 is extended parallel to and over the needles 104.

Figure 7:
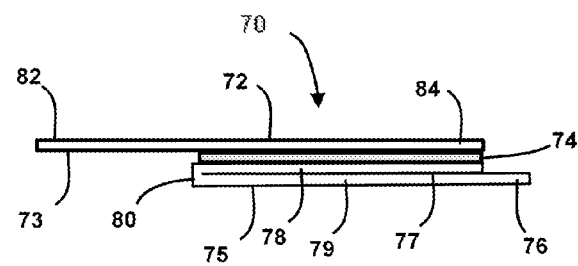
FIG. 7 is a planar side view of an alternative embodiment of a protective flap assembly of the present invention having an adhesive cover adapted for removal from the free end of the protective flap.

The above embodiment requires that the removable protective strip 150 be peeled towards the needle electrode's point of entry into the skin. In the embodiment shown in FIG. 7, a protective flap assembly 70 comprises a protective flap 72 having a layer of adhesive 74 on its skin-facing surface 73. The adhesive layer 74 is covered by a removable adhesive protecting strip 75 which covers the entire adhesive layer. The protecting strip 75 is folded back on itself, and has a first section 78 adjacent to and removably adhering to the adhesive layer 74, and a second section 79 adjacent and parallel to the first section 78 which separates it from the adhesive layer 74. The first 78 and second 79 sections are on opposite sides of the fold 80 which is located proximal to the edge of the adhesive layer closest to the first end portion 82 of the protective flap 72 where the protective flap assembly 70 will be attached to the safety cover of a subdermal needle electrode cable assembly. The first section 78 of the protecting strip 75 only covers the adhesive layer while the second section 79 of the protecting strip 75 extends beyond the adhesive layer 74 and the second end portion 84 of the protective flap 72, the end opposite the first end portion 82 where the protective flap 72 will be attached to the safety cover, to form a tab 76, which may have a width equal to or greater than that of the first section 78 of the protective strip 75 or which may have a reduced width such as the tab 152 shown in FIG. 6A. The second section 79 may be very weakly attached to the first section 78 of the protective strip 75 to prevent it from flapping freely. To remove the protective strip 75 once a needle electrode is in place, the user grasps the tab 76 and pulls away from the needle and fold 80, thereby causing the first section 78 of the protective cover 75 to peel away from the adhesive layer 74 starting from the fold 80 until the protective cover 75 is completely removed. In addition to making removal of the strip covering the adhesive layer 74 easier, this design has the added advantage that the protective flap 72 can start to adhere to the patient's skin before the entire protecting cover 75 is removed which will help maintain sterility, if the adhesive layer 74 is sterile.

In an alternate embodiment, the protecting strip 75 is not folded and a thin strip of material replaces the second section 79. The strip is attached at or proximal to a first end to the first section 78 of the protecting strip 75 where the fold 80 was in the previous embodiment, and then extends beyond the opposite end of the first section 78 past the distal end of the second end portion 84 of the protective flap 72. Pulling on the free end of the thin strip extending beyond the distal end of the second end portion 84 of the protective flap 72 will peel off the protecting strip 75, starting at the first end proximal to where the fold 80 was in the previous embodiment. The thin strip can be weakly attached to the side of the first section 78 of the adhesive protecting strip 75 away from the adhesive layer 74 near its free end, so that it does not flap about, but will still easily separate from the first section 78 when a person pulls on its free end. There may be a tab at the end of the first section 78 proximal to the needle extending beyond the adhesive layer, and the thin strip may be attached to the free end of that. The various embodiments of the protecting strip can be used with any embodiment of the present invention.

Figure 8A:
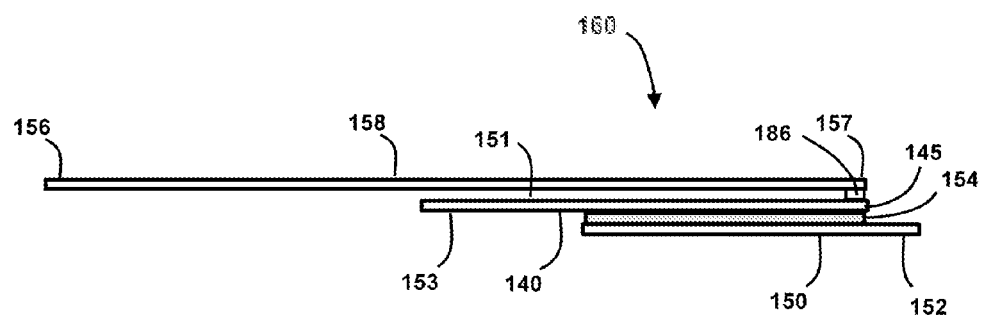
FIG. 8A is a planar side view of an alternative embodiment of a protective flap assembly of the present invention having a pull strip that enables removal of both the protective flap and the needle by pulling on the needle assembly wire.
Figure 8B:
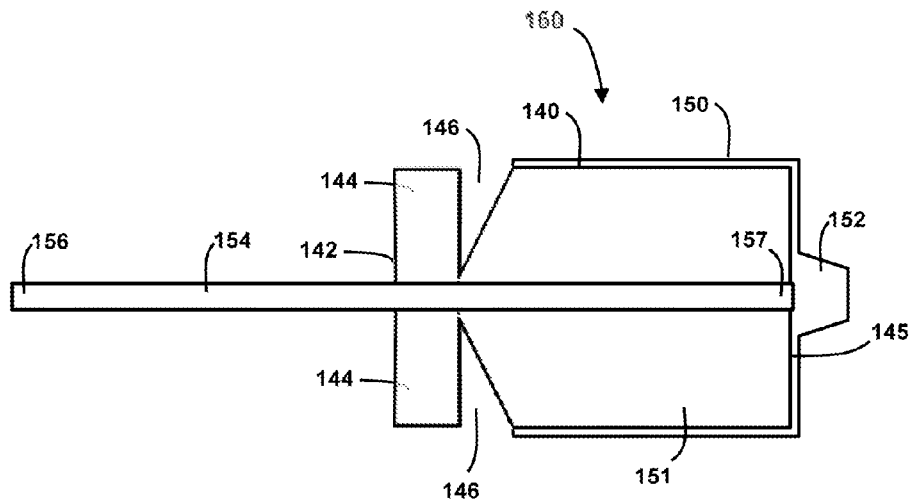
FIG. 8B is a planar top view of the embodiment of a protective flap assembly of the present invention shown in FIG. 8A.

A similar approach can be used to make it easier to remove the subdermal needle electrode cable assembly from the patient. As noted hereinabove, medical technicians often remove subdermal electrode needles by yanking on their wires (e.g., wire 102), for example, by grasping the wire 102 at a distance from the first electrical connector 108, on the second portion of the wire 120, or even at the second electrical connector 110. Referring to FIGS. 8A and 8B, protective flap assembly 160 incorporates the protective flap assembly 141 shown in FIG. 6B described above. Added to this is a pulling strip 158 which is attached at its first end portion 157 to the protective flap 140 at or proximal to its second free end 145 using a known means (the attachment point 186 is shown in FIG. 8A), such as an adhesive, welding, crimping, or the like. The opposite second end 156 of the pulling strip 158 is to be attached to the electrical wire (such as wire 102 of subdermal needle electrode cable assembly 100 in FIG. 3-5) by a known means such as adhesive, wrapping, welding or crimping, preferably proximal to where the wire 102 exits the safety cover 106 at the reduced cross sectional portion 124 (e.g., it is attached to the wire 102 after it is outside of the safety cover 106). When a healthcare worker pulls on the wire 102 to withdraw the needle electrode 104 into the safety cover or retraction chamber 106, he will exert tension on the pulling strip 154, which will transfer the force to the distal end 145 of the protection flap 140, which, if the protection flap 140 is flexible enough, will cause it to peel back and off the skin towards the direction of pull. The safety cover 106 will still be anchored to the patient by the protective flap 140, so as the protective flap 140 peels back the needle electrode 104 will be withdrawn into the safety cover 106. Once the user has pulled the needle electrode 104 completely within the safety cover 106, the protective flap 140 will either be fully or mostly peeled off the skin of the patient, making final removal of the subdermal needle electrode cable assembly 100 from the patient easy and safe, preferably with an additional light tug on the wire 102. If a portion of the protective flap 140 on its skin-facing side 153 adjacent to its second end 145 is adhesive free (for example, roughly the first 0.25, 0.5 or 1 cm), the second end 145 will readily lift and bend backwards when the pulling strip 158 is first pulled upon, facilitating the removal process by beginning the peeling off of the protective flap 140 without having to first overcome the resistance of an adhesive where the peeling starts.

Alternately, a stop may be crimped onto the wire 102 just outside the safety cover 106. The pulling strip 158 is then attached loosely to the wire 102 at a distance from the stop equal to the distance the safety cover 106 must move relative to the wire 102 to fully cover the needle 104 (but less than the total distance the safety cover 106 can move relative to the wire 102). When a medical personnel pulls on the wire 102, the force will first withdraw the needle 104 into the safety cover 106 which will be anchored to the patient's skin by the adhesive protective flap 140. At that point the stop will catch the pulling strip 158, and the force on the wire will start peeling the protective flap 140 off the patient; further pulling will remove it completely.

A small resistance bumper or friction pad may be used in some embodiments of this invention (not shown) to prevent premature and unintended retraction of the needle electrode 104 into the safety cover or retraction chamber 106 into the second position P2. The force to move past this resistance bumper should not exceed the force required to remove the adhesive from the skin, so that the needle electrode 104 can be retracted into the safety cover or retraction chamber 106 while the protective flap 140 is still adherent to the patient's skin, and the protective flap will only begin to be removed once the needle electrode 104 has been fully and safely retracted into the safety cover 106.

When received from the supplier, the neuromonitoring needle assembly can include a needle cover to protect against needle sticks prior to use. Using the subdermal needle electrode cable assembly 100 shown in FIGS. 3 and 4 as an example, the needle cover can take several forms. In one embodiment, the needle cover is tubular, which covers the needle 104 and attaches via friction or some similar means to the first end 123 of the safety cover. In one embodiment, the needle cover is an envelope-like sleeve that covers both the needle 114 and the protective cover 130 and is made of two sheets of material attached at least two opposite edges, or at three. The protective flap 130 and needle 104 are inserted into the needle cover sleeve, covering both. One of the two sheets of material is resistant to needle piercing, and is adjacent to the needle when in place (the other sheet is on the opposite side of the protective flap). The piercing-resistant sheet can have a recess formed in it adapted to accommodate the needle 104 (see FIG. 9A). A tab on which a person can pull to remove the needle cover sleeve can be attached to the end of the sleeve opposite its open end. The sleeve can cover only the needle 114 and protective flap 140, or it can also cover the safety cover 106. It can have an adhesive-bearing tab or pair of tabs that closes around the open end of a sleeve once it is in place like the tab that closes a large envelope. A tear strip or string can be incorporated into the needle cover sleeve to facilitate its removal.

Figure 9A:
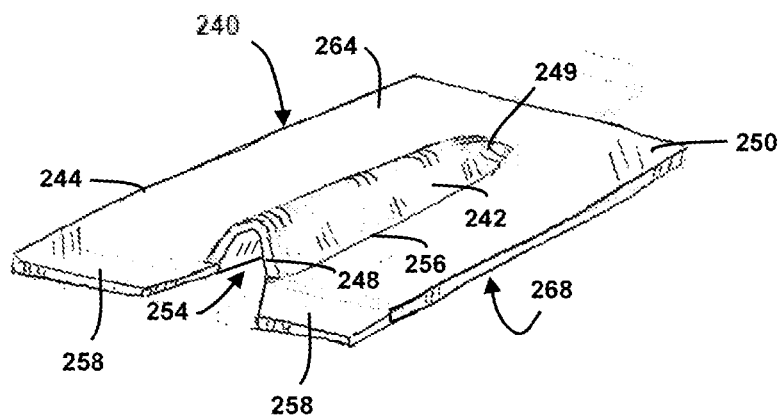
FIG. 9A is a perspective view of a needle cover adapted for attachment to a protective flap of the present invention.
Figure 9B:
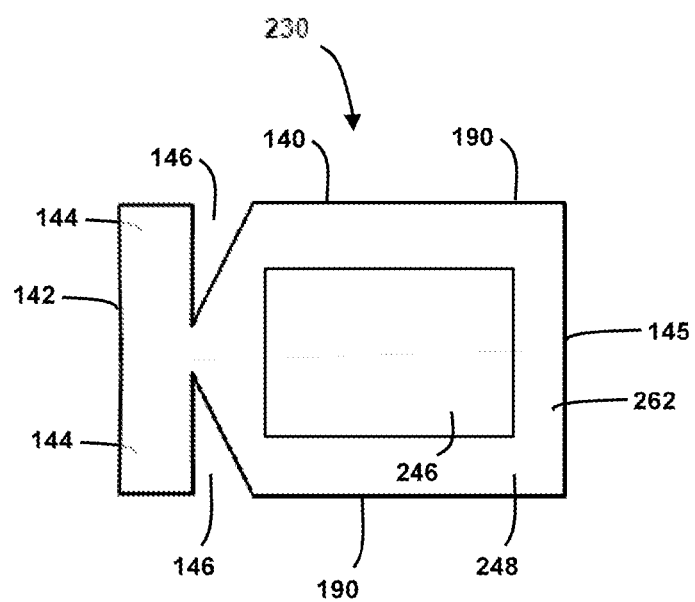
FIG. 9B is a planar bottom view of the adhesive-bearing side of a protective flap assembly for which the adhesive cover shown in FIG. 8A is adapted.

In one embodiment, the protective flap 130 becomes part of the needle cover. A sheet of material covering the needle attaches to the protective flap 130, preferably in such a way that it can easily be torn away, such as by having perforations where the protective flap 130 and the other sheet are attached, or using a weak adhesive to attach them. A version of the latter is shown in FIGS. 9A and 9B. The roughly rectangular needle cover sheet 240 has a roughly semi-cylindrical recess 242 formed into it. The needle cover sheet is about the size of the free portion of the protective flap (e.g., 140) with which it will be used. The recess has a first, open end 248 and a second, closed end 249, and a planar flange 250 extending from the two edges 256 of the recess 242 parallel to its longitudinal axis, and from the second end 249. The second end 249 can be squared off or tapered, although if the recess 242 is long enough, the second end 249 may not need to be closed. A portion of the flange 250 attached along the longitudinal edges 256 of the needle chamber 242 extends beyond the open end 248 of the needle chamber 242 in a direction parallel to the needle chamber's 242 central axis to form two tabs 258 by which the needle cover 240 can be grasped by medical personnel for peeling the needle cover sheet off the protective flap 130 prior to use.

The needle cover 240 has a top side 264 which faces away from the protective flap 140 in use, and a bottom side 268 opposite it. The bottom side 268 has a narrow strip of adhesive (not visible) around its perimeter on the three sides other than the side proximal to the open end 248 of the needle cover. This adhesive strip is for attaching the needle cover 240 to the protective flap 140. The adhesive used is preferably one that will allow the needle cover 240 to easily be peeled off the protective flap 140 such as, for example, the adhesive used for Post-It notes.

The needle chamber 242 is constructed from a material that will resist piercing by a sharp, such as a needle tip. Materials used for prior art needle covers can be used here. The flange 250 can be made from the same material or from a more flexible material, such as those used to cover the adhesive portion of an adhesive bandage. The flange 250 can be thinner material than the needle cover 242 material.

FIG. 9B shows the skin-side of a protective flap assembly 230 configured for use with the needle cover 240 shown in FIG. 9A. The protective flap assembly 230 incorporates the protective flap 140 shown in FIG. 5A. The adhesive layer (not visible) is rectangular and covers only the central section of the protective flap's 140 larger second end 262. Around it is an adhesive free perimeter strip 248 adjacent to the two lateral sides and distal end side 145 of the protective flap 140. The adhesive layer is covered by a removable cover strip 246 as described hereinabove. The narrow strip of adhesive around the perimeter on three sides of the underside 268 of the needle cover is configured to align with and stick to the adhesive free perimeter strip 248 of the protective flap 140.

The needle cover 240 is attached to the protective flap assembly 230 with the recess axially aligned with the needle 104 and its open end 248 proximal to the safety cover 106. The needle 104 will nest within the needle chamber 242 with the safety cover 106 in the first position P1 with at least the first portion 114 of the needle 104 extending beyond the safety cover. In an alternate embodiment, the adhesive layer and the cover strip 246 extend to the lateral and distal edges of the protective flap, and the needle cover 240 adhesive sticks to the top surface of the cover strip 246 (the surface away from the adhesive), which can be relatively nonstick.

While the description above used subdermal needle electrode cable assemblies as the type of needle being used with the protective flap, protective flaps, especially adhesive protective flap assemblies can be incorporated into many other types of needle assemblies, such as the needles used to draw blood donations and needle-cannula assemblies used for intravenous treatments. If the needle is a trocar which is removed after the cannula is in place, the adhesive protective flap assembly can be attached to the cannula or tube, or to a stopcock or connector. If the needle assembly incorporates a butterfly flap for improved gripping, the protective flap or adhesive protective flap assembly can be attached directly to the butterfly flap. In addition, the protective flap can be so designed and attached to the butterfly flaps that gripping and squeezing the two butterfly flaps together will cause the protective flap to lift up and away from the needle (see FIG. 1B). For these needles, the protective flap will be used only to anchor the needle and hold it in place because re-emergence of these needles through the skin is generally not the problem that it is with neuromonitoring needles. If the protective flap 130 does not need to protect against needle sticks (i.e., resist piercing by a needle), it can be made out of any flexible material strong enough to hold the needle in place if the flap 130 is anchored to the skin, including fabric, polymer, or paper, even if that material will not successfully resist piercing by the needle.

Figure 10:
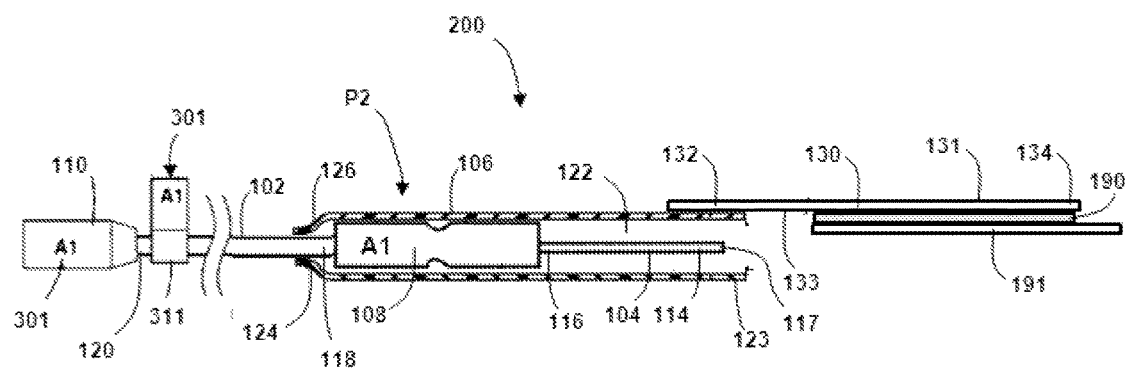
FIG. 10 is a partial cross-sectional side view of the subdermal needle electrode cable assembly shown in FIG. 3 wherein the protective flap has a layer of adhesive on its skin-facing side and a removable protective sheet covering the adhesive.

In a preferred embodiment, the needle assembly 200 shown in FIG. 10, the needle assembly incorporates both a retraction chamber 106 (safety cover) and a protective flap 130. The protective flap 130 preferably is a robust polymer flap which provides impenetrable barrier between needle tip 117 and medical personnel, and is transparent or semi-transparent so the needle entry site is visible. It has an adhesive layer 190 on its skin-facing surface 133 covered by a removable adhesive cover 191 similar to the removable adhesive covers used on adhesive bandages, the protective flap 130 with the adhesive layer 190 operating to secure the protective flap 130 and needle 104 in place. In use, the medical personnel can withdraw the needle 104 from the skin directly into the safety cover 106 by pulling on the wire 102 (with other types of needle assemblies, the wire 102 may be replaced by a tube), and then peel the protective flap 130 off of the patient. The needle tip 117 is never exposed during withdrawal. With the addition of a needle cover, the present invention protects medical personnel performing procedures using or involving needles from needle sticks before the needle is in place, during needle placement, during and after needle removal, AND while the needle is in place in the patient, such as during transfers of a patient from one position to another.

The needle assemblies of the present invention are easy to use, the adhesive flap maintains the needle's position throughout the surgical case, the adhesive flap prevents the needle from being pulled out, eliminating the need to secure the needle with a separate piece of tape, and anchors the needle without levering the needle up as tape tends to do when placed over the exposed portion of the needle assembly base as described hereinabove. Currently no safety device is being used with neuromonitoring needle electrodes. Hundreds of thousands of surgical cases using neuromonitoring are performed annually, and the present invention will protect the medical workers on those cases from the currently all-too-frequent needle stick injuries that put their health at risk. In addition, incorporating an adhesive anchoring flap into needles used for purposes other than neuromonitoring, such as venous blood collection needles or IV needles, provides a safe, integrated and convenient way to anchor those needles in place during use.

Figure 11:
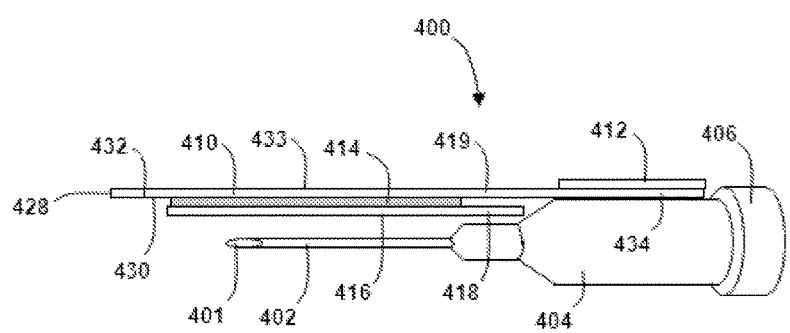
FIG. 11 is side perspective view of an IV needle assembly configured in accordance with an embodiment of the present invention incorporating a butterfly flap for gripping and a protective flap.

FIG. 11 shows a needle assembly 400 configured according to the present invention, with one end of a hollow needle 402 attached to a first end of a needle assembly body 404 and the other end 401 of the needle 402 adapted for piercing. A connector 406 is attached to the other end of the needle assembly body 404. The connector 406 provides a means for attaching a tube to transport liquids to or from the needle, and can include a valve. Attached to the needle assembly body 404 at a first end portion 434 is a rectangular anchoring flap 410, which extends from the needle assembly body 404 in the direction of the needle tip 401, preferably with its longitudinal centerline aligned with the needle 402.

The anchoring flap 410 can be rectangular, oblong, polygonal, trapezoidal or some other shape. The lateral dimension (width) of the anchoring flap 410 proximal to its second end portion 432 is preferably similar to that of surgical tap, such as 1, 2, 3, 4 or 5 cm. The length of the free portion 433 of the anchoring flap 410 (from the first end portion where it is attached to the body 404 to its distal end 428) is preferably at least as long as the needle 402, such as 2, 3, 4, 5, 6, 7, 8 or 10 cm. Preferably, the anchoring flap 410 extends to or beyond the tip of the needle 401.

The anchoring flap 410 has an adhesive layer 414 on a portion of the anchoring flap's 410 bottom side 430 (the side facing the needle 402) between where its first end 434 and its second end portion 432, with the end portion 432 being free from adhesive so that it can act as a tab medical personnel can grasp to remove the anchoring flap 410 from the patient. The adhesive layer 414 is completely covered by a cover strip 416 which can be made of any of the materials currently used to cover adhesive strips such as adhesive bandages and double-sided picture mounting tape. The cover strip 416 extends beyond the adhesive layer 414 at least at one end to create a tab 418 for medical personnel to grasp for exposing the adhesive layer 414. The anchoring flap 410 is made of a flexible but resilient material, such as paper, thin polymer or fabric, and can be made from the type of materials used for surgical tapes and adhesive bandages).

Attached to the top side 419 (opposite the bottom side) of the anchoring flap 410 above the needle assembly body 404 is an optional butterfly-type grip (the anchoring flap 410 is situated between the butterfly flap 412 and the needle assembly body 404), which is made of any of the materials currently or in the future in use for butterfly flaps for needles.

Figure 12:
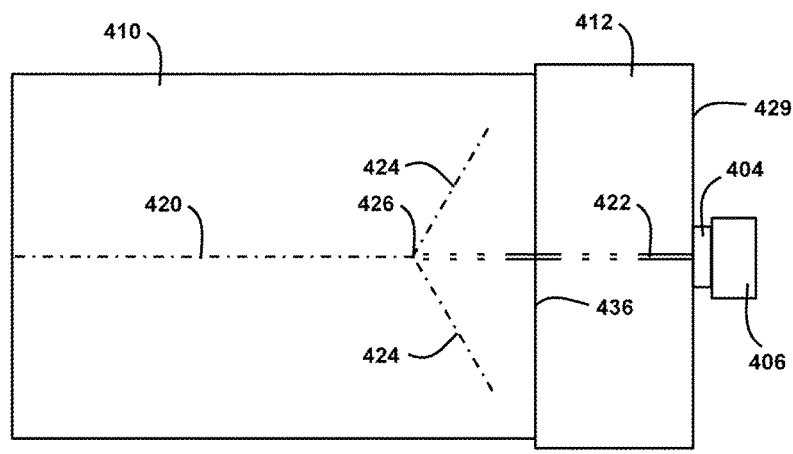
FIG. 12 is a planar view of the top of the needle assembly shown in FIG. 11 showing pre-folds in the protective flap that causes the free end of the protective flap to lift up and away from the needle when the butterfly flap is pressed down upon.

FIG. 12 is a top view of the needle assembly 400 in FIG. 11. To grip the needle assembly 400 for insertion of the needle 402 into a patient, one pushes the butterfly flaps 412 down and around the needle assembly body 404. If creases are appropriately preformed in the anchoring flap 410, and optionally in the butterfly flap 412, the free end 433 of the anchoring flap 410 will lift up and away from the needle 402 and back towards a user's hand when the user pushes the butterfly flaps 412 down and around the needle assembly body 404, thereby moving the anchoring flap 410 out of the way so that the needle 402 is clearly visible and unobstructed for insertion into the patient. Release of the butterfly flaps 412 will cause the anchoring flap 410 to unfold back into its planar configuration, positioned over the needle 402, especially if the butterfly flaps 412 are constructed of a resilient material that springs back from its folded position into a planar configuration with some force. The cover strip 416 can be removed to expose the adhesive layer 414 while the anchoring flap 410 is folded back and before it returns to its rest position parallel to the needle 402. The exposed adhesive layer 414 can then be pressed down onto the patient's skin, thereby anchoring the needle assembly 400 to the patient.

One embodiment of a pre-creased anchoring flap 410 is shown in FIG. 12. Four preformed creases meet at a point 426 centered over the central axis of the needle 402 and needle assembly body 404 and proximal to the first end portion 434, but partially towards the free distal end 428 of the anchoring flap 410 (as shown, this point of intersection 426 is proximal to where the needle 402 and the needle assembly body 404 join). The creases shown with a line consisting of one long dash followed by a short dash are pre-folded for folding upwards away from the needle 402, and the crease shown with a double line consisting of one long dash followed by two short dashes is pre-bent for folding downwards towards the needle assembly body 404. There is a first upward-folded crease 420 running from the middle of the free distal end 428 of the anchoring flap 410 at its second end portion 432 to the intersection point 426, the crease running parallel to and over the needle 402. A second downward crease 422 is in line with the first crease 420 and runs from the intersection point 426 to the center of the opposite end 429 of the anchoring flap 410 at its first end portion 434. Two downward creases 424 start at the intersection point 426 and run at obtuse angles to the first crease 420. These two downward creases 424 may run to the edge of the anchoring flap 410 or only partway to the edge. The angled creases 424 preferably intersect, or would intersect if extended, the edge of the anchoring flap 410 between the needle-side edge 436 of the butterfly flap 412 and where a line from the intersection point 426 perpendicular to the first crease 420 would intersect the edges of the anchoring flap 410. The absolute obtuse angle between the first crease 420 and each of these two creases 424 will depend upon the design of the needle assembly 400, and in the embodiment shown in FIG. 12 is about 120 degrees, but can be smaller or larger depending upon the width of the anchoring flap 410, its length, where the butterfly flap 412 is attached to it, and the position of the butterfly flap 410 and anchoring flap 412 on the needle assembly body 404. For example, the obtuse angles can range from about 110 degrees to about 140 degrees.

Figure 13:
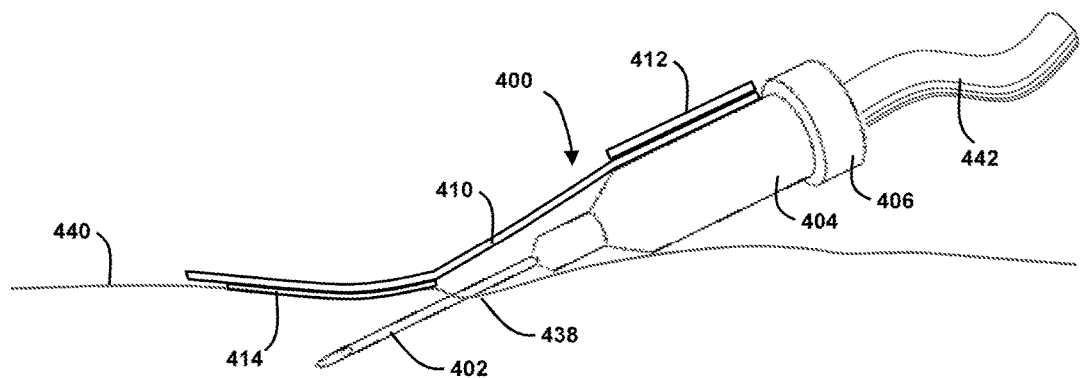
FIG. 13 is a perspective side view of the needle assembly shown in FIG. 11 inserted into a patient's skin and secured in place by a protective flap.

FIG. 13 shows the needle assembly 400 with the needle 402 placed through a patient's skin 440, with the adhesive layer 414 of the anchoring flap 410 adhering to the patient's skin 440 and securing the needle assembly 400 to the patient. A tube 442 is attached to the connector 406 of the needle assembly 400. The adhesive layer 414 can be sized to cover the point of entry 438 of the needle 402 into the skin 440. There can be a patch of gauze-type material, preferably sterile, surrounded by the adhesive layer, attached to the skin-side 30 of the anchoring flap 410 to provide an adhesive bandage-like dressing over the point of entry 438. The anchoring flap 410 may be designed to separate easily so that its bandage-like end can remain in place over the point of needle entry 438 after the needle 402 is withdrawn.

Some needle assemblies for fluid administration or collection have safety features to prevent needle sticks. In some cases, there is a safety cover that covers the needle after use that is similar to the safety cover 106 in FIG. 3. In an embodiment of the present invention incorporating such as needle assembly, the protective flap is attached to the safety cover. Other safety needle assemblies are constructed so that the needle retracts directly into the body of the assembly (e.g., body 404 in FIG. 11). In an embodiment of the present invention incorporating such as needle assembly, the protective flap is attached to the body. The protective flap or anchoring flap can be attached to whatever part of the needle assembly is appropriate for accomplishing the purpose for which it was designed (e.g., protect against re-emerging needles, anchor the needle in the patient).

A sample of devices that are described herein are as follows:

A safety needle assembly comprising a needle having a base end and a tip, a body attached at a first end to the base end of the needle, and a flap attached at a first end to the body, the flap having a second distal free end capable of extending beyond the tip of the needle.

The safety needle assembly of the above paragraph, wherein said needle is a needle electrode.

The safety needle assembly of the above paragraph, wherein the body comprises an electrically conductive assembly comprising an electrical connector attached at a first end to the base end of the needle and an electrically conductive wire attached to a second end of the electrical connector, the electrical connector operating to electrically connect the needle and the wire.

The safety needle assembly of the above paragraph, wherein the flap is movably attached to the electrically conductive assembly.

The safety needle assembly, wherein the needle is hollow, the body comprises a tube having a fluidic connection at a first end to the needle and having a connector adapted to make a fluidic connection at a second end.

The safety needle assembly, further comprising an adhesive layer on a first side of the flap adjacent to the needle.

The safety needle assembly of the above paragraph, further comprising a removable sheet of material covering the adhesive layer.

The safety needle assembly, wherein a first portion of the flap incorporating the second distal end of the flap is made of a material resistant to piercing by a needle.

The safety needle assembly of the above paragraph, wherein the first portion of the flap is substantially centered over the tip of the needle when the flap is extended from where it is attached to the body over and parallel to the needle.

The safety needle assembly of the above paragraph, wherein the first portion of the flap has an area at least equal to that of a circle having a radius of between about one-quarter the length of the needle and the length of the needle.

A safety needle assembly comprising a needle having a base end and a tip, a body attached at a first end to the base end of the needle, a safety cover movably attached to the body, and a flap attached at a first end to the safety cover, the flap having a second distal free end capable of extending beyond the tip of the needle.

The safety needle assembly of the above paragraph, wherein said needle is a needle electrode.

The safety needle assembly of the above paragraph, wherein the body comprises an electrical connector attached at a first end to the base end of the needle and an electrically conductive wire attached to a second end of the electrical connector, the electrical connector operating to electrically connect the needle and the wire.

The safety needle assembly, wherein the safety cover comprises a central passage configured to receive the needle therein; and wherein the safety cover is movable between a first position in which the tip of the needle electrode is exposed outside of the central passage and a second position in which the tip of the needle becomes positioned within the central passage.

The safety needle assembly, wherein the needle is hollow, the body is a tube having a fluidic connection at a first end to the needle and having a connector adapted to make a fluidic connection at a second end.

The safety needle assembly, further comprising an adhesive layer on a first side of the flap adjacent to the needle.

The safety needle assembly of the above paragraph, further comprising a removable sheet of material covering the adhesive layer.

The safety needle assembly, wherein a first portion of the flap incorporating the second distal end of the flap is made of a material resistant to piercing by a needle The safety needle assembly of the above paragraph, wherein the first portion of the flap is substantially centered over the tip of the needle when the flap is extended from its attachment point to the safety cover over and parallel to the needle.

The safety needle assembly of the above paragraph, wherein the first portion of the flap has an area at least equal to that of a circle having a radius of between about one-quarter the length of the needle and the length of the needle.

Further modifications and alternative embodiments of various aspects of the invention may be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims. In addition, it is to be understood that features described herein independently may, in certain embodiments, be combined.

What is claimed is:

1. A safety needle assembly comprising:
    a needle having a base end and a tip;
    a body attached at a first end to the base end of the needle; and
    a flap attached at a first end to the body, the flap having a second distal free end,
    wherein:
        a first portion of the flap is made of a material resistant to piercing by the needle, and
        when the flap is extended parallel to and over the needle, the first portion of the flap is substantially centered laterally over the needle transverse to the axis of the needle,
        the first portion of the flap extends beyond the tip of the needle a distance at least equal to the smaller of one centimeter or one-quarter the length of the needle,
        the first portion of the flap has a width at least equal to the smaller of one centimeter and one-quarter the length of the needle, and
        the first portion of the flap has an area at least equal to the smaller of a circle having a diameter of one centimeter and a circle having a radius of one-quarter the length of the needle.

2. The safety needle assembly of claim 1, wherein said needle is a needle electrode.

3. The safety needle assembly of claim 2, wherein the body comprises an electrically conductive assembly, the electrically conductive assembly comprising an electrical connector and an electrically conductive wire, the electrical connector having a first end and a second end, wherein the first end of the electrical connector is attached to the base end of the needle and wherein the second end of the electrical connector is attached to the electrically conductive wire, the electrical connector operating to electrically connect the needle and the electrically conductive wire.

4. The safety needle assembly of claim 3, wherein the flap is movably attached to the electrically conductive assembly.

5. The safety needle assembly of claim 1, wherein the needle is hollow, the body comprises a tube having a fluidic connection at a first end to the needle and having a connector adapted to make a fluidic connection at a second end.

6. The safety needle assembly of claim 1, further comprising an adhesive layer on a first side of the flap adjacent to the needle.

7. The safety needle assembly of claim 6, further comprising a removable sheet of material covering the adhesive layer.

8. The safety needle assembly of claim 1, wherein the flap is transparent or semi-transparent.

9. A safety needle assembly comprising a needle having a base end and a tip, a body attached at a first end to the base end of the needle, a safety cover movably attached to the body, and a flap attached at a first end to the safety cover, the flap having a second distal free end, wherein:
    a first portion of the flap is made of a material resistant to piercing by the needle, and
    when the flap is extended parallel to and over the needle, the first portion of the flap is substantially centered laterally over the needle transverse to the axis of the needle,
    the first portion of the flap extends beyond the tip of the needle a distance at least equal to the smaller of one centimeter or one-quarter the length of the needle,
    the first portion of the flap has a width at least equal to the smaller of one centimeter and one-quarter the length of the needle, and
    the first portion of the flap has an area at least equal to the smaller of a circle having a diameter of one centimeter and a circle having a radius of one-quarter the length of the needle.

10. The safety needle assembly of claim 9, wherein said needle is a needle electrode.

11. The safety needle assembly of claim 10, wherein the body comprises an electrical connector and an electrically conductive wire, the electrical connector having a first end and a second end, wherein the first end of the electrical connector is attached to the base end of the needle and wherein the second end of the electrical connector is attached to the electrically conductive wire, the electrical connector operating to electrically connect the needle and the electrically conductive wire.

12. The safety needle assembly of claim 9, wherein the safety cover comprises a central passage configured to receive the needle therein; and wherein the safety cover is movable between a first position in which the tip of the needle electrode is exposed outside of the central passage and a second position in which the tip of the needle becomes positioned within the central passage.

13. The safety needle assembly of claim 9, wherein the needle is hollow, the body is a tube having a fluidic connection at a first end to the needle and having a connector adapted to make a fluidic connection at a second end.

14. The safety needle assembly of claim 9, further comprising an adhesive layer on a first side of the flap adjacent to the needle.

15. The safety needle assembly of claim 14, further comprising a removable sheet of material covering the adhesive layer.

16. The safety needle assembly of claim 9, wherein the flap is transparent or semi-transparent.

* * * * *

UNITED STATES PATENT AND TRADEMARK OFFICE
CERTIFICATE OF CORRECTION

| | | |
|---|---|---|
| PATENT NO. | : 9,968,271 B2 | Page 1 of 1 |
| APPLICATION NO. | : 14/381440 | |
| DATED | : May 15, 2018 | |
| INVENTOR(S) | : Padalino et al. | |

It is certified that error appears in the above-identified patent and that said Letters Patent is hereby corrected as shown below:

Column 22, Claim number 1, Line 7, please delete "or" and replace with "and".

Column 22, Claim number 9, Line 54, please delete "or" and replace with "and".

Signed and Sealed this
Fourteenth Day of August, 2018

Andrei Iancu
*Director of the United States Patent and Trademark Office*